US008910639B2

(12) United States Patent
Chang et al.

(10) Patent No.: US 8,910,639 B2
(45) Date of Patent: Dec. 16, 2014

(54) SINGLE-USE CONNECTOR AND CARTRIDGE FOR A SMOKING ARTICLE AND RELATED METHOD

(75) Inventors: Yi-Ping Chang, Greensboro, NC (US); Charles Jacob Novak, III, Winston-Salem, NC (US)

(73) Assignee: R. J. Reynolds Tobacco Company, Winston-Salem, NC (US)

( * ) Notice: Subject to any disclaimer, the term of this patent is extended or adjusted under 35 U.S.C. 154(b) by 296 days.

(21) Appl. No.: 13/603,612

(22) Filed: Sep. 5, 2012

(65) Prior Publication Data

US 2014/0060555 A1 Mar. 6, 2014

(51) Int. Cl.
*A24F 47/00* (2006.01)
*A24F 7/02* (2006.01)
*A61M 15/06* (2006.01)

(52) U.S. Cl.
USPC ....................... 131/273; 131/225; 128/202.21

(58) Field of Classification Search
CPC ....................................................... A24F 7/02
USPC ....................................... 128/200.14–207.18
See application file for complete search history.

(56) References Cited

U.S. PATENT DOCUMENTS

| | | | |
|---|---|---|---|
| 922,543 | A | 5/1909 | Truston |
| 1,771,366 | A | 7/1930 | Wyss et al. |
| 2,057,353 | A | 10/1936 | Whittemore, Jr. |
| 2,104,266 | A | 1/1938 | McCormick |
| 2,805,669 | A | 9/1957 | Meriro |
| 3,200,819 | A | 8/1965 | Gilbert |
| 3,316,919 | A | 5/1967 | Green et al. |
| 3,398,754 | A | 8/1968 | Tughan |
| 3,419,015 | A | 12/1968 | Wochnowski |
| 3,424,171 | A | 1/1969 | Rooker |
| 3,476,118 | A | 11/1969 | Luttich |
| 4,054,145 | A | 10/1977 | Berndt et al. |

(Continued)

FOREIGN PATENT DOCUMENTS

| | | |
|---|---|---|
| AU | 276250 | 7/1965 |
| CA | 2 752 255 | 8/2010 |

(Continued)

OTHER PUBLICATIONS

U.S. Appl. No. 13/205,841, filed Aug. 9, 2011, Worm.

(Continued)

*Primary Examiner* — Richard Crispino
*Assistant Examiner* — Eric Yaary
(74) *Attorney, Agent, or Firm* — Womble Carlyle Sandridge & Rice, LLP

(57) ABSTRACT

The present disclosure relates to connectors that may be employed in cartridges for smoking articles. The connectors may include a single-use mechanism that may include a blocking pin, a biasing mechanism, and a release mechanism. The release mechanism may hold the blocking pin in a partially retracted position in which the blocking pin is at least partially retracted from an aperture extending through threads defined by the connector. The release mechanism may include a latch that is displaced from contact with the blocking pin by a release pin upon engagement of the connector with a mating connector. The biasing mechanism may force the blocking pin against an end of the mating connector such that when the mating connector is unscrewed from the connector, the blocking pin extends through the aperture and blocks at least one recess defined between the threads such that the connector may not be reused.

9 Claims, 11 Drawing Sheets

(56) References Cited

U.S. PATENT DOCUMENTS

| | | | |
|---|---|---|---|
| 4,131,117 | A | 12/1978 | Kite et al. |
| 4,150,677 | A | 4/1979 | Osborne |
| 4,190,046 | A | 2/1980 | Virag |
| 4,219,032 | A | 8/1980 | Tabatznik et al. |
| 4,259,970 | A | 4/1981 | Green, Jr. |
| 4,284,089 | A | 8/1981 | Ray |
| 4,303,083 | A | 12/1981 | Burruss, Jr. |
| 4,449,541 | A | 5/1984 | Mays et al. |
| 4,506,682 | A | 3/1985 | Muller |
| 4,635,651 | A | 1/1987 | Jacobs |
| 4,674,519 | A | 6/1987 | Keritsis et al. |
| 4,708,151 | A | 11/1987 | Shelar |
| 4,714,082 | A | 12/1987 | Banerjee et al. |
| 4,735,217 | A | 4/1988 | Gerth et al. |
| 4,756,318 | A | 7/1988 | Clearman et al. |
| 4,771,795 | A | 9/1988 | White et al. |
| 4,776,353 | A | 10/1988 | Lilja et al. |
| 4,793,365 | A | 12/1988 | Sensabaugh, Jr. et al. |
| 4,800,903 | A | 1/1989 | Ray et al. |
| 4,819,665 | A | 4/1989 | Roberts et al. |
| 4,821,749 | A | 4/1989 | Toft et al. |
| 4,830,028 | A | 5/1989 | Lawson et al. |
| 4,836,224 | A | 6/1989 | Lawson et al. |
| 4,836,225 | A | 6/1989 | Sudoh |
| 4,848,374 | A | 7/1989 | Chard et al. |
| 4,848,376 | A | 7/1989 | Lilja et al. |
| 4,874,000 | A | 10/1989 | Tamol et al. |
| 4,880,018 | A | 11/1989 | Graves, Jr. et al. |
| 4,887,619 | A | 12/1989 | Burcham, Jr. et al. |
| 4,907,606 | A | 3/1990 | Lilja et al. |
| 4,913,168 | A | 4/1990 | Potter et al. |
| 4,917,119 | A | 4/1990 | Potter et al. |
| 4,917,128 | A | 4/1990 | Clearman et al. |
| 4,922,901 | A | 5/1990 | Brooks et al. |
| 4,924,888 | A | 5/1990 | Perfetti et al. |
| 4,928,714 | A | 5/1990 | Shannon |
| 4,938,236 | A | 7/1990 | Banerjee et al. |
| 4,941,483 | A | 7/1990 | Ridings et al. |
| 4,941,484 | A | 7/1990 | Clapp et al. |
| 4,945,931 | A | 8/1990 | Gori |
| 4,947,874 | A | 8/1990 | Brooks et al. |
| 4,947,875 | A | 8/1990 | Brooks et al. |
| 4,972,854 | A | 11/1990 | Kiernan et al. |
| 4,972,855 | A | 11/1990 | Kuriyama et al. |
| 4,986,286 | A | 1/1991 | Roberts et al. |
| 4,987,906 | A | 1/1991 | Young et al. |
| 5,005,593 | A | 4/1991 | Fagg |
| 5,019,122 | A | 5/1991 | Clearman et al. |
| 5,022,416 | A | 6/1991 | Watson |
| 5,042,510 | A | 8/1991 | Curtiss et al. |
| 5,056,537 | A | 10/1991 | Brown et al. |
| 5,060,669 | A | 10/1991 | White et al. |
| 5,060,671 | A | 10/1991 | Counts et al. |
| 5,065,775 | A | 11/1991 | Fagg |
| 5,072,744 | A | 12/1991 | Luke et al. |
| 5,074,319 | A | 12/1991 | White et al. |
| 5,076,296 | A | 12/1991 | Nystrom et al. |
| 5,093,894 | A | 3/1992 | Deevi et al. |
| 5,095,921 | A | 3/1992 | Losee et al. |
| 5,097,850 | A | 3/1992 | Braunshteyn et al. |
| 5,099,862 | A | 3/1992 | White et al. |
| 5,099,864 | A | 3/1992 | Young et al. |
| 5,103,842 | A | 4/1992 | Strang et al. |
| 5,121,757 | A | 6/1992 | White et al. |
| 5,129,409 | A | 7/1992 | White et al. |
| 5,131,415 | A | 7/1992 | Munoz et al. |
| 5,143,097 | A | 9/1992 | Sohn et al. |
| 5,144,962 | A | 9/1992 | Counts et al. |
| 5,146,934 | A | 9/1992 | Deevi et al. |
| 5,159,940 | A | 11/1992 | Hayward et al. |
| 5,159,942 | A | 11/1992 | Brinkley et al. |
| 5,179,966 | A | 1/1993 | Losee et al. |
| 5,211,684 | A | 5/1993 | Shannon et al. |
| 5,220,930 | A | 6/1993 | Gentry |
| 5,224,498 | A | 7/1993 | Deevi et al. |
| 5,228,460 | A | 7/1993 | Sprinkel, Jr. et al. |
| 5,230,354 | A | 7/1993 | Smith et al. |
| 5,235,992 | A | 8/1993 | Sensabaugh |
| 5,243,999 | A | 9/1993 | Smith |
| 5,246,018 | A | 9/1993 | Deevi et al. |
| 5,249,586 | A | 10/1993 | Morgan et al. |
| 5,261,424 | A | 11/1993 | Sprinkel, Jr. |
| 5,269,327 | A | 12/1993 | Counts et al. |
| 5,285,798 | A | 2/1994 | Banerjee et al. |
| 5,293,883 | A | 3/1994 | Edwards |
| 5,301,694 | A | 4/1994 | Raymond |
| 5,303,720 | A | 4/1994 | Banerjee et al. |
| 5,318,050 | A | 6/1994 | Gonzalez-Parra et al. |
| 5,322,075 | A | 6/1994 | Deevi et al. |
| 5,322,076 | A | 6/1994 | Brinkley et al. |
| 5,326,207 | A | 7/1994 | Cerny |
| 5,339,838 | A | 8/1994 | Young et al. |
| 5,345,951 | A | 9/1994 | Serrano et al. |
| 5,353,813 | A | 10/1994 | Deevi et al. |
| 5,357,984 | A | 10/1994 | Farrier et al. |
| 5,360,023 | A | 11/1994 | Blakley et al. |
| 5,369,723 | A | 11/1994 | Counts et al. |
| 5,372,148 | A | 12/1994 | McCafferty et al. |
| 5,377,698 | A | 1/1995 | Litzinger et al. |
| 5,388,574 | A | 2/1995 | Ingebrethsen et al. |
| 5,388,594 | A | 2/1995 | Counts et al. |
| 5,408,574 | A | 4/1995 | Deevi et al. |
| 5,435,325 | A | 7/1995 | Clapp et al. |
| 5,445,169 | A | 8/1995 | Brinkley et al. |
| 5,468,266 | A | 11/1995 | Bensalem et al. |
| 5,468,936 | A | 11/1995 | Deevi et al. |
| 5,479,948 | A | 1/1996 | Counts et al. |
| 5,498,850 | A | 3/1996 | Das |
| 5,498,855 | A | 3/1996 | Deevi et al. |
| 5,499,636 | A | 3/1996 | Baggett, Jr. et al. |
| 5,501,237 | A | 3/1996 | Young et al. |
| 5,505,214 | A | 4/1996 | Collins et al. |
| 5,530,225 | A | 6/1996 | Hajaligol |
| 5,551,450 | A | 9/1996 | Hemsley |
| 5,551,451 | A | 9/1996 | Riggs et al. |
| 5,564,442 | A | 10/1996 | MacDonald et al. |
| 5,573,692 | A | 11/1996 | Das et al. |
| 5,591,368 | A | 1/1997 | Fleischhauer et al. |
| 5,593,792 | A | 1/1997 | Farrier et al. |
| 5,595,577 | A | 1/1997 | Bensalem et al. |
| 5,595,706 | A | 1/1997 | Sikka et al. |
| 5,611,360 | A | 3/1997 | Tang |
| 5,613,504 | A | 3/1997 | Collins et al. |
| 5,613,505 | A | 3/1997 | Campbell et al. |
| 5,649,552 | A | 7/1997 | Cho et al. |
| 5,649,554 | A | 7/1997 | Sprinkel et al. |
| 5,659,656 | A | 8/1997 | Das |
| 5,665,262 | A | 9/1997 | Hajaligol et al. |
| 5,666,976 | A | 9/1997 | Adams et al. |
| 5,666,977 | A | 9/1997 | Higgins et al. |
| 5,666,978 | A | 9/1997 | Counts et al. |
| 5,692,525 | A | 12/1997 | Counts et al. |
| 5,692,526 | A | 12/1997 | Adams et al. |
| 5,708,258 | A | 1/1998 | Counts et al. |
| 5,711,320 | A | 1/1998 | Martin |
| 5,726,421 | A | 3/1998 | Fleischhauer et al. |
| 5,727,571 | A | 3/1998 | Meiring et al. |
| 5,730,158 | A | 3/1998 | Collins et al. |
| 5,750,964 | A | 5/1998 | Counts et al. |
| 5,799,663 | A | 9/1998 | Gross et al. |
| 5,816,263 | A | 10/1998 | Counts et al. |
| 5,819,756 | A | 10/1998 | Mielordt |
| 5,829,453 | A | 11/1998 | White et al. |
| 5,865,185 | A | 2/1999 | Collins et al. |
| 5,865,186 | A | 2/1999 | Volsey, II |
| 5,878,752 | A | 3/1999 | Adams et al. |
| 5,880,439 | A | 3/1999 | Deevi et al. |
| 5,915,387 | A | 6/1999 | Baggett, Jr. et al. |
| 5,934,289 | A | 8/1999 | Watkins et al. |
| 5,954,979 | A | 9/1999 | Counts et al. |
| 5,967,148 | A | 10/1999 | Harris et al. |
| 6,026,820 | A | 2/2000 | Baggett, Jr. et al. |
| 6,033,623 | A | 3/2000 | Deevi et al. |
| 6,040,560 | A | 3/2000 | Fleischhauer et al. |

(56) References Cited

U.S. PATENT DOCUMENTS

| | | | |
|---|---|---|---|
| 6,053,176 | A | 4/2000 | Adams et al. |
| 6,089,857 | A | 7/2000 | Matsuura et al. |
| 6,095,153 | A | 8/2000 | Kessler et al. |
| 6,116,247 | A | 9/2000 | Banyasz et al. |
| 6,119,700 | A | 9/2000 | Fleischhauer et al. |
| 6,125,853 | A | 10/2000 | Susa et al. |
| 6,125,855 | A | 10/2000 | Nevett et al. |
| 6,125,866 | A | 10/2000 | Nichols et al. |
| 6,155,268 | A | 12/2000 | Takeuchi |
| 6,164,287 | A | 12/2000 | White |
| 6,182,670 | B1 | 2/2001 | White |
| 6,196,218 | B1 | 3/2001 | Voges |
| 6,216,706 | B1 | 4/2001 | Kumar et al. |
| 6,289,898 | B1 | 9/2001 | Fournier et al. |
| 6,349,728 | B1 | 2/2002 | Pham |
| 6,357,671 | B1 | 3/2002 | Cewers |
| 6,418,938 | B1 | 7/2002 | Fleischhauer et al. |
| 6,446,426 | B1 | 9/2002 | Sweeney et al. |
| 6,532,965 | B1 | 3/2003 | Abhulimen et al. |
| 6,598,607 | B2 | 7/2003 | Adiga et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,701,936 | B2 | 3/2004 | Shafer et al. |
| 6,715,494 | B1 | 4/2004 | McCoy |
| 6,730,832 | B1 | 5/2004 | Dominguez et al. |
| 6,772,756 | B2 | 8/2004 | Shayan |
| 6,803,545 | B2 | 10/2004 | Blake et al. |
| 6,803,550 | B2 | 10/2004 | Sharpe et al. |
| 6,810,883 | B2 | 11/2004 | Felter et al. |
| 6,854,461 | B2 | 2/2005 | Nichols et al. |
| 6,854,470 | B1 | 2/2005 | Pu |
| 6,994,096 | B2 | 2/2006 | Rostami et al. |
| 7,011,096 | B2 | 3/2006 | Li et al. |
| 7,017,585 | B2 | 3/2006 | Li et al. |
| 7,025,066 | B2 | 4/2006 | Lawson et al. |
| 7,117,867 | B2 | 10/2006 | Cox et al. |
| 7,163,015 | B2 | 1/2007 | Moffitt |
| 7,173,222 | B2 | 2/2007 | Cox et al. |
| 7,185,659 | B2 | 3/2007 | Sharpe et al. |
| 7,234,470 | B2 | 6/2007 | Yang |
| 7,290,549 | B2 | 11/2007 | Banerjee et al. |
| 7,293,565 | B2 | 11/2007 | Griffin et al. |
| 7,392,809 | B2 | 7/2008 | Larson et al. |
| 7,513,253 | B2 | 4/2009 | Kobayashi et al. |
| 7,647,932 | B2 | 1/2010 | Cantrell et al. |
| 7,690,385 | B2 | 4/2010 | Moffitt |
| 7,692,123 | B2 | 4/2010 | Baba et al. |
| 7,726,320 | B2 | 6/2010 | Robinson et al. |
| 7,810,505 | B2 | 10/2010 | Yang |
| 7,832,410 | B2 | 11/2010 | Hon |
| 7,878,209 | B2 | 2/2011 | Newbery et al. |
| 7,896,006 | B2 | 3/2011 | Hamano et al. |
| 8,066,010 | B2 | 11/2011 | Newbery et al. |
| 8,079,371 | B2 | 12/2011 | Robinson et al. |
| 2002/0146242 | A1 | 10/2002 | Vieira |
| 2003/0131859 | A1 | 7/2003 | Li et al. |
| 2004/0020500 | A1 | 2/2004 | Wrenn et al. |
| 2004/0129280 | A1 | 7/2004 | Woodson et al. |
| 2004/0149296 | A1 | 8/2004 | Rostami et al. |
| 2004/0200488 | A1 | 10/2004 | Felter et al. |
| 2004/0226568 | A1 | 11/2004 | Takeuchi et al. |
| 2004/0255965 | A1 | 12/2004 | Perfetti et al. |
| 2005/0016549 | A1 | 1/2005 | Banerjee et al. |
| 2005/0066986 | A1 | 3/2005 | Nestor et al. |
| 2005/0172976 | A1 | 8/2005 | Newman et al. |
| 2005/0274390 | A1 | 12/2005 | Banerjee et al. |
| 2006/0016453 | A1 | 1/2006 | Kim |
| 2006/0070633 | A1 | 4/2006 | Rostami et al. |
| 2006/0162733 | A1 | 7/2006 | McGrath et al. |
| 2006/0185687 | A1 | 8/2006 | Hearn et al. |
| 2006/0196518 | A1 | 9/2006 | Hon |
| 2007/0074734 | A1 | 4/2007 | Braunshteyn et al. |
| 2007/0102013 | A1 | 5/2007 | Adams et al. |
| 2007/0215167 | A1 | 9/2007 | Crooks et al. |
| 2007/0283972 | A1 | 12/2007 | Monsees et al. |
| 2008/0092912 | A1 | 4/2008 | Robinson et al. |
| 2008/0149118 | A1 | 6/2008 | Oglesby et al. |
| 2008/0245377 | A1 | 10/2008 | Marshall et al. |
| 2008/0257367 | A1 | 10/2008 | Paterno et al. |
| 2008/0276947 | A1 | 11/2008 | Martzel |
| 2008/0302374 | A1 | 12/2008 | Wengert et al. |
| 2009/0065010 | A1 | 3/2009 | Shands |
| 2009/0095311 | A1 | 4/2009 | Hon |
| 2009/0095312 | A1 | 4/2009 | Herbrich et al. |
| 2009/0126745 | A1 | 5/2009 | Hon |
| 2009/0188490 | A1 | 7/2009 | Han |
| 2009/0230117 | A1 | 9/2009 | Fernando et al. |
| 2009/0260641 | A1 | 10/2009 | Monsees et al. |
| 2009/0260642 | A1 | 10/2009 | Monsees et al. |
| 2009/0272379 | A1 | 11/2009 | Thorens et al. |
| 2009/0283103 | A1 | 11/2009 | Nielsen et al. |
| 2009/0293892 | A1 | 12/2009 | Williams et al. |
| 2009/0320863 | A1 | 12/2009 | Fernando et al. |
| 2009/0324206 | A1 | 12/2009 | Young et al. |
| 2010/0006113 | A1 | 1/2010 | Urtsev et al. |
| 2010/0024834 | A1 | 2/2010 | Oglesby et al. |
| 2010/0043809 | A1 | 2/2010 | Magnon |
| 2010/0059070 | A1 | 3/2010 | Potter et al. |
| 2010/0059073 | A1 | 3/2010 | Hoffmann et al. |
| 2010/0065075 | A1 | 3/2010 | Banerjee et al. |
| 2010/0083959 | A1 | 4/2010 | Siller |
| 2010/0163063 | A1 | 7/2010 | Fernando et al. |
| 2010/0200006 | A1 | 8/2010 | Robinson et al. |
| 2010/0200008 | A1 | 8/2010 | Taieb |
| 2010/0229881 | A1 | 9/2010 | Hearn |
| 2010/0242974 | A1 | 9/2010 | Pan |
| 2010/0242976 | A1 | 9/2010 | Katayama et al. |
| 2010/0258139 | A1 | 10/2010 | Onishi et al. |
| 2010/0300467 | A1 | 12/2010 | Kuistila et al. |
| 2010/0307518 | A1 | 12/2010 | Wang |
| 2010/0313901 | A1 | 12/2010 | Fernando et al. |
| 2011/0005535 | A1 | 1/2011 | Xiu |
| 2011/0011396 | A1 | 1/2011 | Fang |
| 2011/0036363 | A1 | 2/2011 | Urtsev et al. |
| 2011/0036365 | A1 | 2/2011 | Chong et al. |
| 2011/0073121 | A1 | 3/2011 | Levin et al. |
| 2011/0088707 | A1 | 4/2011 | Hajaligol |
| 2011/0094523 | A1 | 4/2011 | Thorens et al. |
| 2011/0120482 | A1 | 5/2011 | Brenneise |
| 2011/0126848 | A1 | 6/2011 | Zuber et al. |
| 2011/0155153 | A1 | 6/2011 | Thorens et al. |
| 2011/0155718 | A1 | 6/2011 | Greim et al. |
| 2011/0162663 | A1 | 7/2011 | Bryman |
| 2011/0168194 | A1 | 7/2011 | Hon |
| 2011/0180082 | A1 | 7/2011 | Banerjee et al. |
| 2011/0265806 | A1 | 11/2011 | Alarcon et al. |
| 2011/0277760 | A1 | 11/2011 | Terry et al. |
| 2011/0309157 | A1 | 12/2011 | Yang et al. |
| 2012/0042885 | A1 | 2/2012 | Stone et al. |
| 2012/0060853 | A1 | 3/2012 | Robinson et al. |
| 2012/0111347 | A1 | 5/2012 | Hon |
| 2012/0279512 | A1 | 11/2012 | Hon |
| 2013/0228191 | A1 * | 9/2013 | Newton ........................ 131/329 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 102006041042 | 3/2008 |
| EP | 0 295 122 | 12/1988 |
| EP | 0 430 566 | 6/1991 |
| EP | 0 845 220 | 6/1998 |
| EP | 1618803 | 1/2006 |
| EP | 2 468 116 | 6/2012 |
| GB | 1444461 | 7/1976 |
| GB | 2469850 | 11/2010 |
| WO | WO 86/02528 | 5/1986 |
| WO | WO 97/48293 | 12/1997 |
| WO | WO 02/37990 | 5/2002 |

(56) References Cited

FOREIGN PATENT DOCUMENTS

| | | |
|---|---|---|
| WO | WO 2004/043175 | 5/2004 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO 2010/073122 | 7/2011 |
| WO | WO 2011/081558 | 7/2011 |

OTHER PUBLICATIONS

U.S. Appl. No. 13/432,406, filed Mar. 28, 2012, Griffith, Jr.
U.S. Appl. No. 13/536,438, filed Jun. 28, 2012, Sebastian.
U.S. Appl. No. 13/602,871, filed Sep. 4, 2012, Collett.
International Search Report and Written Opinion of the International Searching Authority for corresponding International Application No. PCT/US2013/056639 mailed Jan. 2, 2014.

* cited by examiner

SINGLE-USE CONNECTOR AND CARTRIDGE FOR A SMOKING ARTICLE AND RELATED METHOD

FIELD OF THE DISCLOSURE

The present disclosure relates to single-use connectors, and more particularly to single-use connectors for use in cartridges that may hold a product which, when employed with aerosol delivery articles, may yield tobacco components or other materials in an inhalable form. The product may be made or derived from tobacco or otherwise incorporate tobacco for human consumption.

BACKGROUND

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Numerous references have proposed various smoking articles of a type that generate flavored vapor, visible aerosol, or a mixture of flavored vapor and visible aerosol. Some of those proposed types of smoking articles include tubular sections or longitudinally extending air passageways.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco.

General examples of alternative smoking articles are described in U.S. Pat. No. 3,258,015 to Ellis et al.; U.S. Pat. No. 3,356,094 to Ellis et al.; U.S. Pat. No. 3,516,417 to Moses; U.S. Pat. No. 4,347,855 to Lanzellotti et al.; U.S. Pat. No. 4,340,072 to Bolt et al.; U.S. Pat. No. 4,391,285 to Burnett et al.; U.S. Pat. No. 4,917,121 to Riehl et al.; U.S. Pat. No. 4,924,886 to Litzinger; and U.S. Pat. No. 5,060,676 to Hearn et al. Many of those types of smoking articles have employed a combustible fuel source that is burned to provide an aerosol and/or to heat an aerosol-forming material. See, for example, the background art cited in U.S. Pat. No. 4,714,082 to Banerjee et al. and U.S. Pat. No. 4,771,795 to White et al.; which are incorporated herein by reference in their entireties. See, also, for example, those types of smoking articles described in U.S. Pat. No. 4,756,318 to Clearman et al.; U.S. Pat. No. 4,714,082 to Banerjee et al.; U.S. Pat. No. 4,771,795 to White et al.; U.S. Pat. No. 4,793,365 to Sensabaugh et al.; U.S. Pat. No. 4,917,128 to Clearman et al.; U.S. Pat. No. 4,961,438 to Korte; U.S. Pat. No. 4,966,171 to Serrano et al.; U.S. Pat. No. 4,969,476 to Bale et al.; U.S. Pat. No. 4,991,606 to Serrano et al.; U.S. Pat. No. 5,020,548 to Farrier et al.; U.S. Pat. No. 5,033,483 to Clearman et al.; U.S. Pat. No. 5,040,551 to Schlatter et al.; U.S. Pat. No. 5,050,621 to Creighton et al.; U.S. Pat. No. 5,065,776 to Lawson; U.S. Pat. No. 5,076,296 to Nystrom et al.; U.S. Pat. No. 5,076,297 to Farrier et al.; U.S. Pat. No. 5,099,861 to Clearman et al.; U.S. Pat. No. 5,105,835 to Drewett et al.; U.S. Pat. No. 5,105,837 to Barnes et al.; U.S. Pat. No. 5,115,820 to Hauser et al.; U.S. Pat. No. 5,148,821 to Best et al.; U.S. Pat. No. 5,159,940 to Hayward et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,240,014 to Deevi et al.; U.S. Pat. No. 5,240,016 to Nichols et al.; U.S. Pat. No. 5,345,955 to Clearman et al.; U.S. Pat. No. 5,551,451 to Riggs et al.; U.S. Pat. No. 5,595,577 to Bensalem et al.; U.S. Pat. No. 5,819,751 to Barnes et al.; U.S. Pat. No. 6,089,857 to Matsuura et al.; U.S. Pat. No. 6,095,152 to Beven et al; U.S. Pat. No. 6,578,584 Beven; and U.S. Pat. No. 6,730,832 to Dominguez; which are incorporated herein by reference in their entireties. Furthermore, certain types of cigarettes that employ carbonaceous fuel elements have been commercially marketed under the brand names "Premier" and "Eclipse" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). See also U.S. Pat. Pub. No. 2005/0274390 to Banerjee et al., U.S. Pat. Pub. No. 2007/0215167 to Crooks et al., U.S. Pat. Pub. No. 2010/0065075 to Banerjee et al., and U.S. Pat. Pub. No. 2012/0042885 to Stone et al., the disclosures of which are incorporated herein by reference in their entireties.

Certain proposed cigarette-shaped tobacco products purportedly employ tobacco in a form that is not intended to be burned to any significant degree. See, for example, U.S. Pat. No. 4,836,225 to Sudoh; U.S. Pat. No. 4,972,855 to Kuriyama et al.; and U.S. Pat. No. 5,293,883 to Edwards, which are incorporated herein by reference in their entireties. Yet other types of smoking articles, such as those types of smoking articles that generate flavored vapors by subjecting tobacco or processed tobaccos to heat produced from chemical or electrical heat sources, are described in U.S. Pat. No. 4,848,374 to Chard et al.; U.S. Pat. Nos. 4,947,874 and 4,947,875 to Brooks et al.; U.S. Pat. No. 5,060,671 to Counts et al.; U.S. Pat. No. 5,146,934 to Deevi et al.; U.S. Pat. No. 5,224,498 to Deevi; U.S. Pat. No. 5,285,798 to Banerjee et al.; U.S. Pat. No. 5,357,984 to Farrier et al.; U.S. Pat. No. 5,593,792 to Farrier et al.; U.S. Pat. No. 5,369,723 to Counts; U.S. Pat. No. 5,692,525 to Counts et al.; U.S. Pat. No. 5,865,185 to Collins et al.; U.S. Pat. No. 5,878,752 to Adams et al.; U.S. Pat. No. 5,880,439 to Deevi et al.; U.S. Pat. No. 5,915,387 to Baggett et al.; U.S. Pat. No. 5,934,289 to Watkins et al.; U.S. Pat. No. 6,033,623 to Deevi et al.; U.S. Pat. No. 6,053,176 to Adams et al.; U.S. Pat. No. 6,164,287 to White; U.S. Pat. No. 6,289,898 to Fournier et al.; U.S. Pat. No. 6,615,840 to Fournier et al.; U.S. Pat. Pub. No. 2003/0131859 to Li et al.; U.S. Pat. Pub. No. 2005/0016549 to Banerjee et al.; and U.S. Pat. Pub. No. 2006/0185687 to Hearn et al., each of which is incorporated herein by reference in its entirety.

Certain attempts have been made to deliver vapors, sprays or aerosols, such as those possessing or incorporating flavors and/or nicotine. See, for example, the types of devices set forth in U.S. Pat. No. 4,190,046 to Virag; U.S. Pat. No. 4,284,089 to Ray; U.S. Pat. No. 4,635,651 to Jacobs; U.S. Pat. No. 4,735,217 to Gerth et al.; U.S. Pat. No. 4,800,903 to Ray et al.; U.S. Pat. No. 5,388,574 to Ingebrethsen et al.; U.S. Pat. No. 5,799,663 to Gross et al.; U.S. Pat. No. 6,532,965 to Abhulimen et al.; and U.S. Pat. No. 6,598,607 to Adiga et al; and EP 1,618,803 to Hon; which are incorporated herein by reference in their entireties. See also, U.S. Pat. No. 7,117,867 to Cox et al. and the devices set forth on the website, www.e-cig.com, which are incorporated herein by reference in their entireties.

Still further representative cigarettes or smoking articles that have been described and, in some instances, been made commercially available include those described in U.S. Pat. No. 4,922,901 to Brooks et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon. See also U.S. Pat. No. D657,047 to Minskoff et al. and U.S. Pat. Pub. Nos. 2011/0277757, 2011/0277760, and U.S. 2011/0277764 to Terry et al. Still further examples include electronic cigarette products commercially available under the names ACCORD®; HEATBAR™; HYBRID CIGARETTE®, VEGAS™; E-GAR™; C-GAR™; E-MYSTICK™; IOLITE® Vaporizer, GREEN SMOKE®, BLU™ Cigs, WHITE CLOUD® Cirrus, V2CIGS™, SOUTH BEACH SMOKE™, SMOKETIP®, SMOKE STIK®, NJOY®, LUCI®, Royal Blues, SMART SMOKER®, SMOKE ASSIST®, Knight Sticks, GAMUCCI®, InnoVapor, SMOKING EVERYWHERE®, Crown 7, CHOICE™ NO.7™, VAPORKING®, EPUFFER®, LOGIC™ ecig, VAPOR4LIFE®, NICOTEK®, METRO®, VUSE®, and PREMIUM™.

However, advances with respect to cartridges for storing and releasing products for use with an electronic smoking article may be desirable.

BRIEF SUMMARY

The present disclosure provides a smoking article and related components and methods. In particular, disclosed herein is a single-use connector. The connector may comprise a body defining a plurality of threads, a plurality of recesses respectively positioned between the threads, and an aperture extending through one or more of the threads. The connector may also include a single-use mechanism. The single-use mechanism may comprise a blocking pin configurable between a retracted position in which the blocking pin is at least partially retracted from the aperture and an extended position in which the blocking pin extends through the aperture and blocks at least one of the recesses. The single-use mechanism may additionally include a biasing mechanism configured to bias the blocking pin toward the extended position and a release mechanism configured to retain the blocking pin in the retracted position and release the blocking pin after the threads and the recesses engage a mating connector.

In some embodiment the threads and the recesses may be defined at an inner surface of the body surrounding a cavity configured to receive the mating connector, whereas in other embodiments the threads and the recesses may be defined at an outer surface of the body and configured to be received in a cavity defined by the mating connector. The release mechanism may comprise a latch configured to engage the blocking pin to retain the blocking pin in the retracted position and a release pin configured to release the latch from engagement with the blocking pin. The blocking pin may define a head and the latch may be configured to engage the head of the blocking pin and pivot out of contact therewith upon being displaced by the release pin. The release pin may define a tapered end configured to engage the latch. The release pin may be configured to engage an end of the mating connector when the threads and the recesses engage the mating connector. Further, the biasing mechanism may comprise a coil spring.

In an additional aspect, a single-use cartridge is provided. The single-use cartridge may comprise a chamber configured to hold a product and a connector. For example, the connector may comprise an embodiment of the connector described above. The product may comprise an aerosol precursor composition in some embodiments. An electronic smoking article comprising the single-use cartridge is also provided.

In a further aspect, a method for assembling a connector is provided. The method may include providing a body defining a plurality of threads, a plurality of recesses, and an aperture extending through one or more of the threads. The method may additionally include providing a single-use mechanism comprising a blocking pin, a release mechanism, and a biasing mechanism. Further, the method may include coupling the single-use mechanism to the body such that the blocking pin is in a retracted position wherein the blocking pin is at least partially retracted from the aperture by the release mechanism, wherein upon disengagement of the threads and recesses from a mating connector the release mechanism releases the blocking pin and the biasing mechanism biases the blocking pin to an extended configuration in which the blocking pin extends through the aperture and blocks at least one of the recesses.

In some embodiments of the method, coupling the single-use mechanism to the body may comprise coupling a coil spring to the body and the blocking pin. Coupling the single-use mechanism to the body may further comprise retracting the blocking pin to the retracted position and engaging the blocking pin with a latch. Additionally, coupling the single-use mechanism to the body may further comprise positioning a release pin in an extended position configured to engage the mating connector and release the latch from the blocking pin upon engagement therewith.

BRIEF DESCRIPTION OF THE FIGURES

Figure 1:
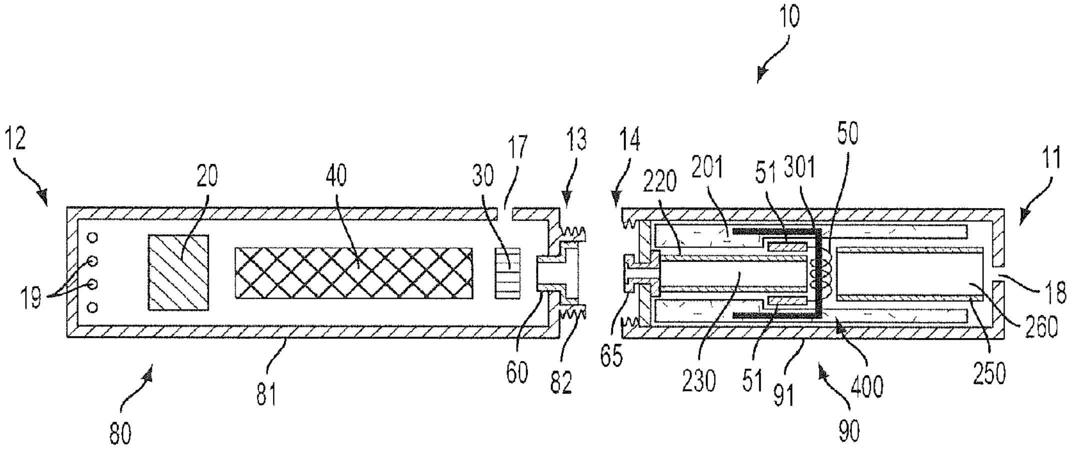
Figure 2:
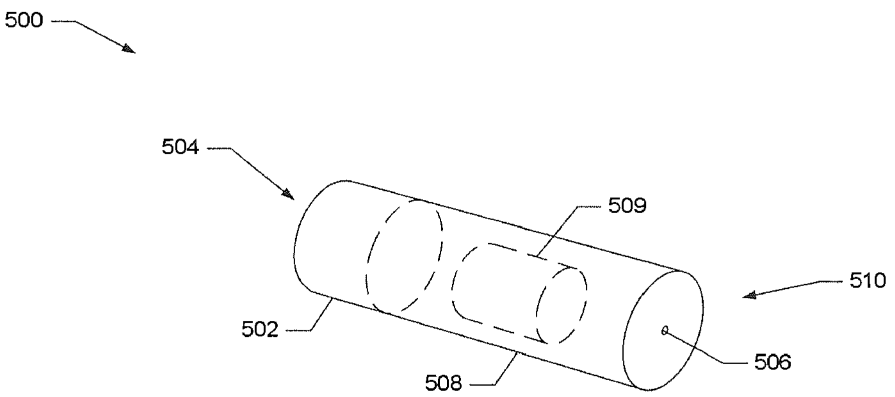
Figure 3:
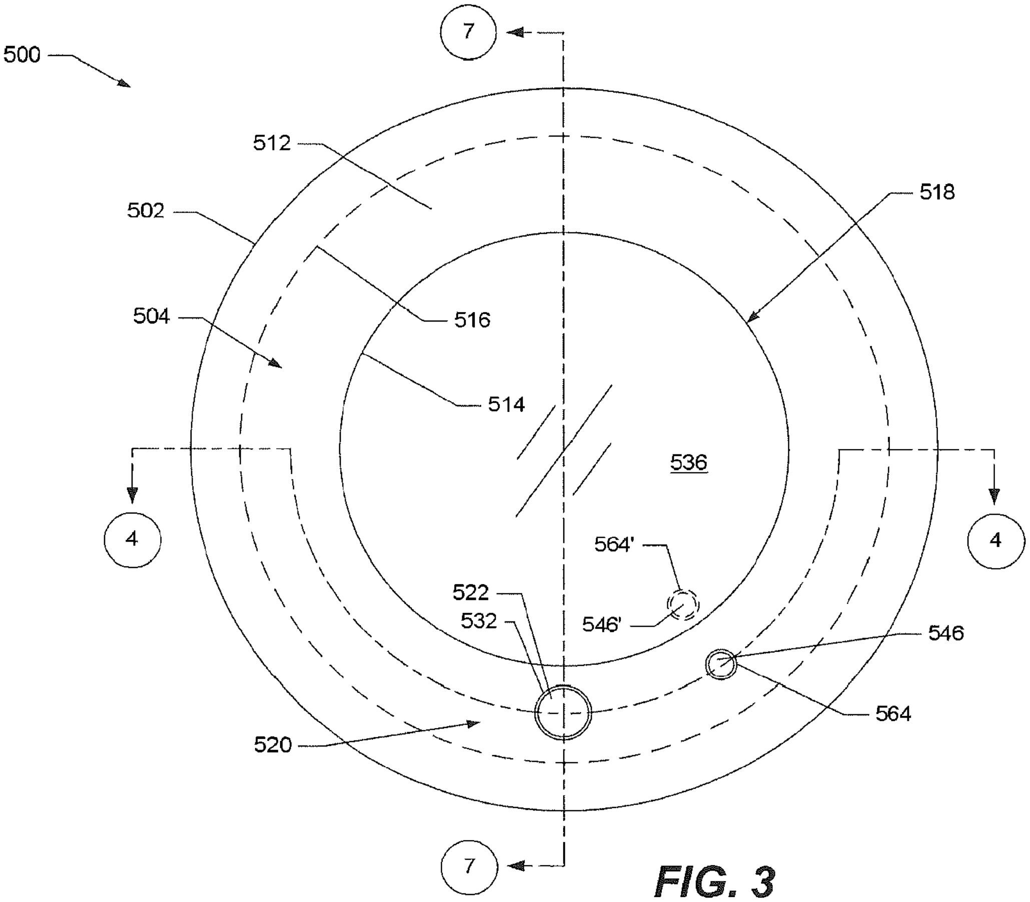
Figure 4:
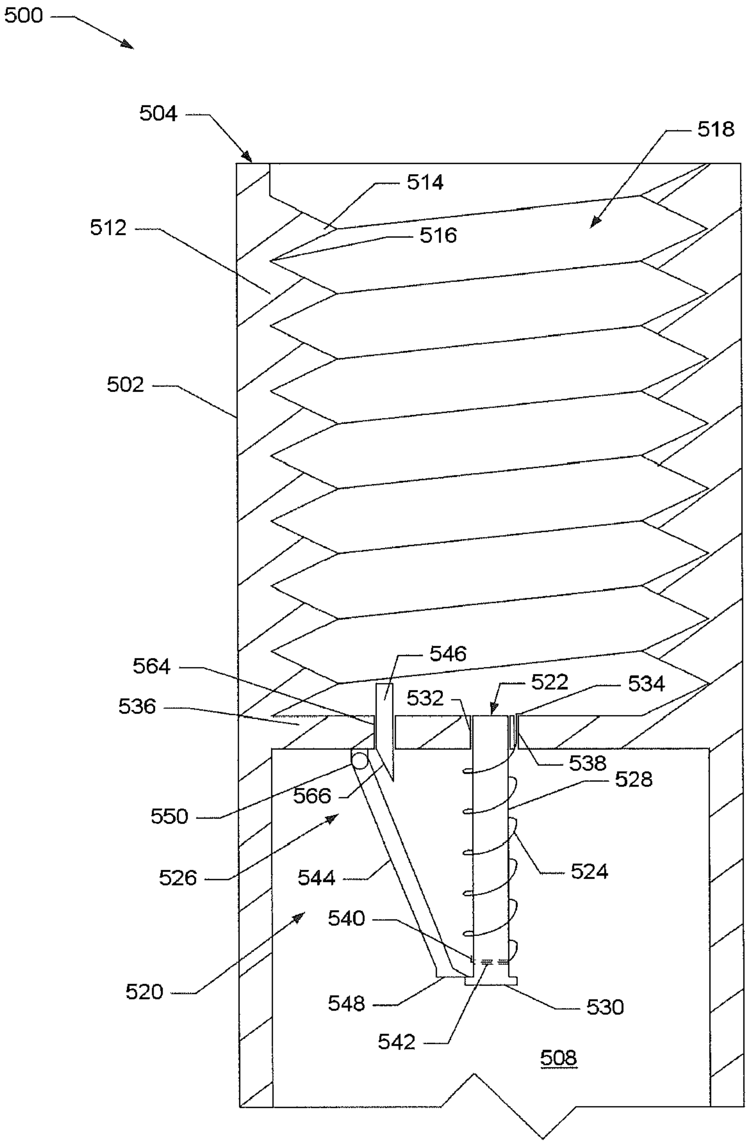
Figure 5:
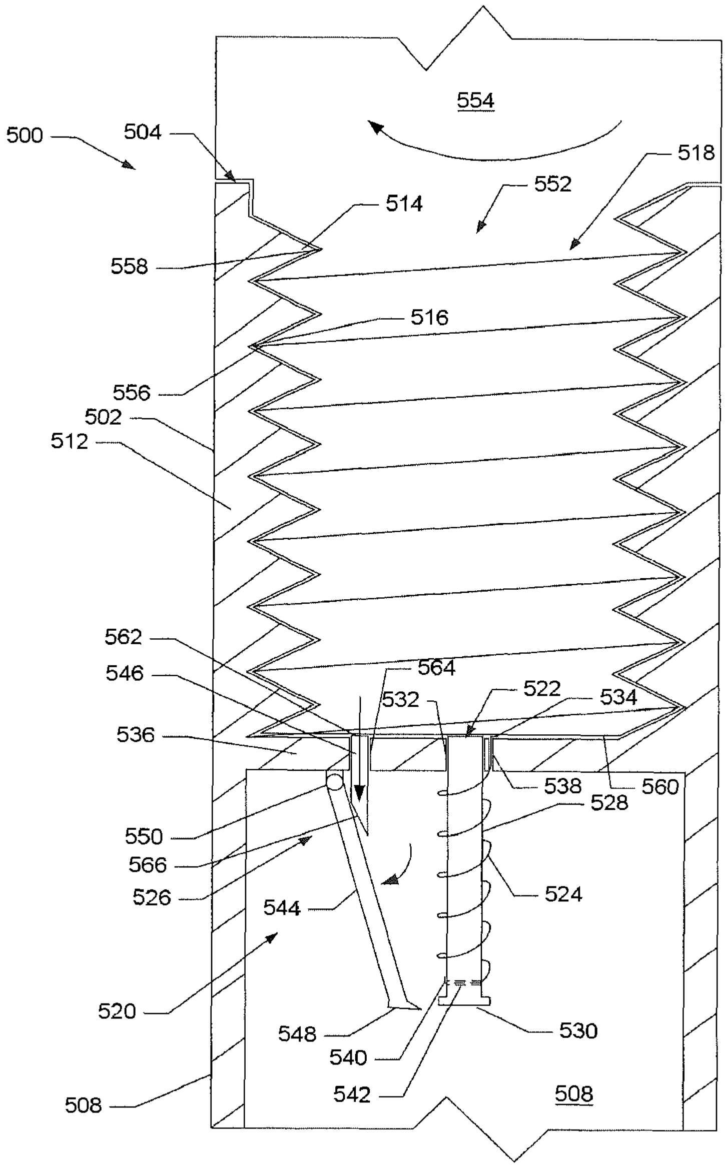
Figure 6:
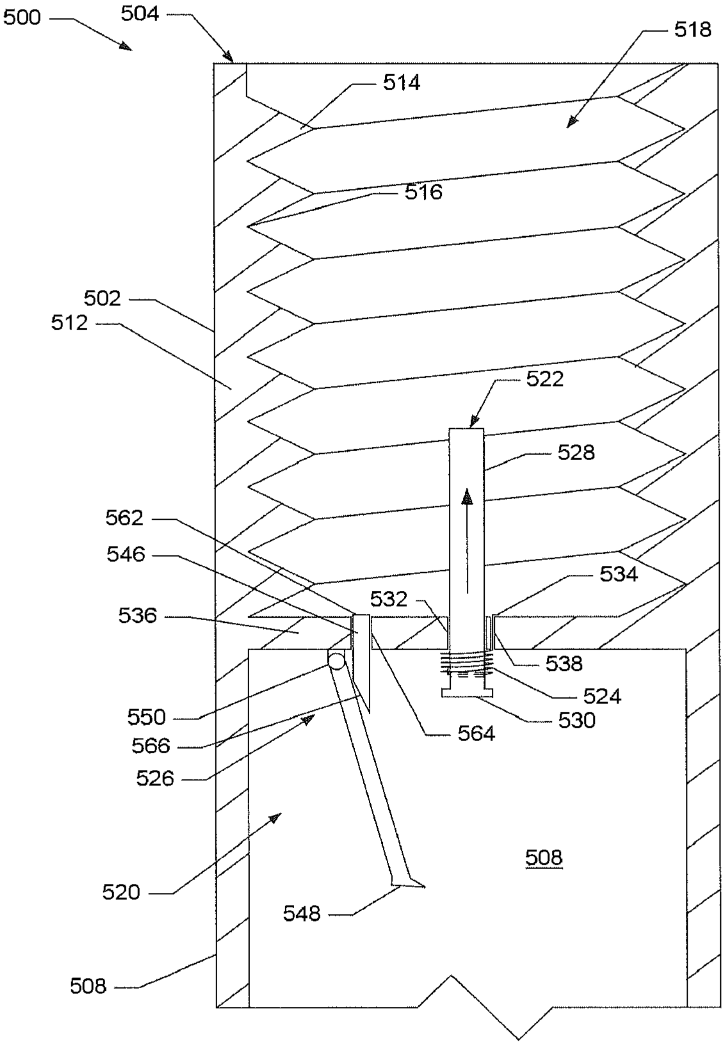
Figure 7:
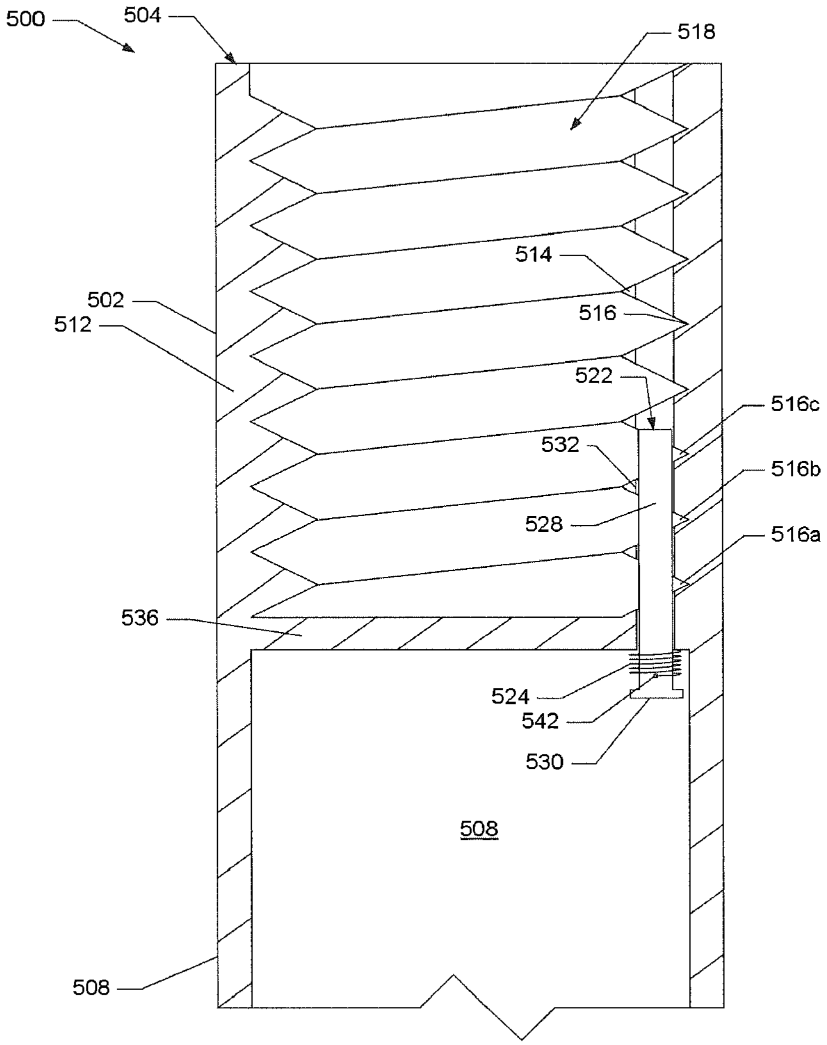
Figure 8:
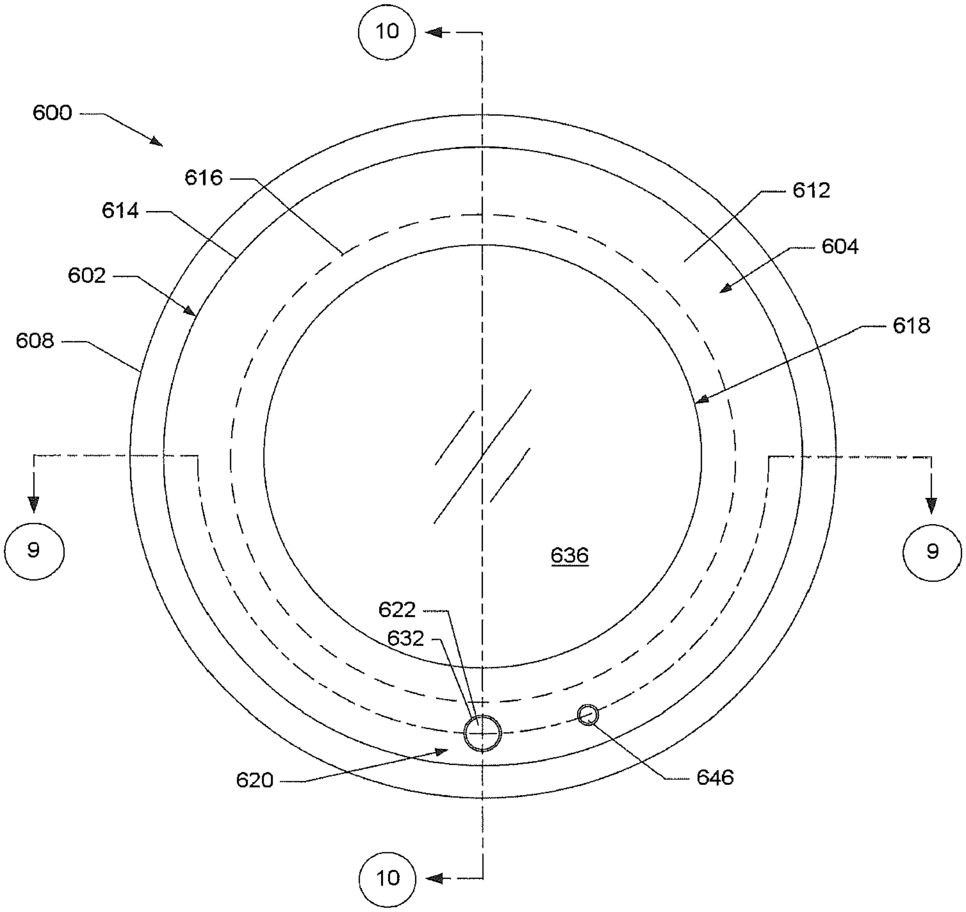
Figure 9:
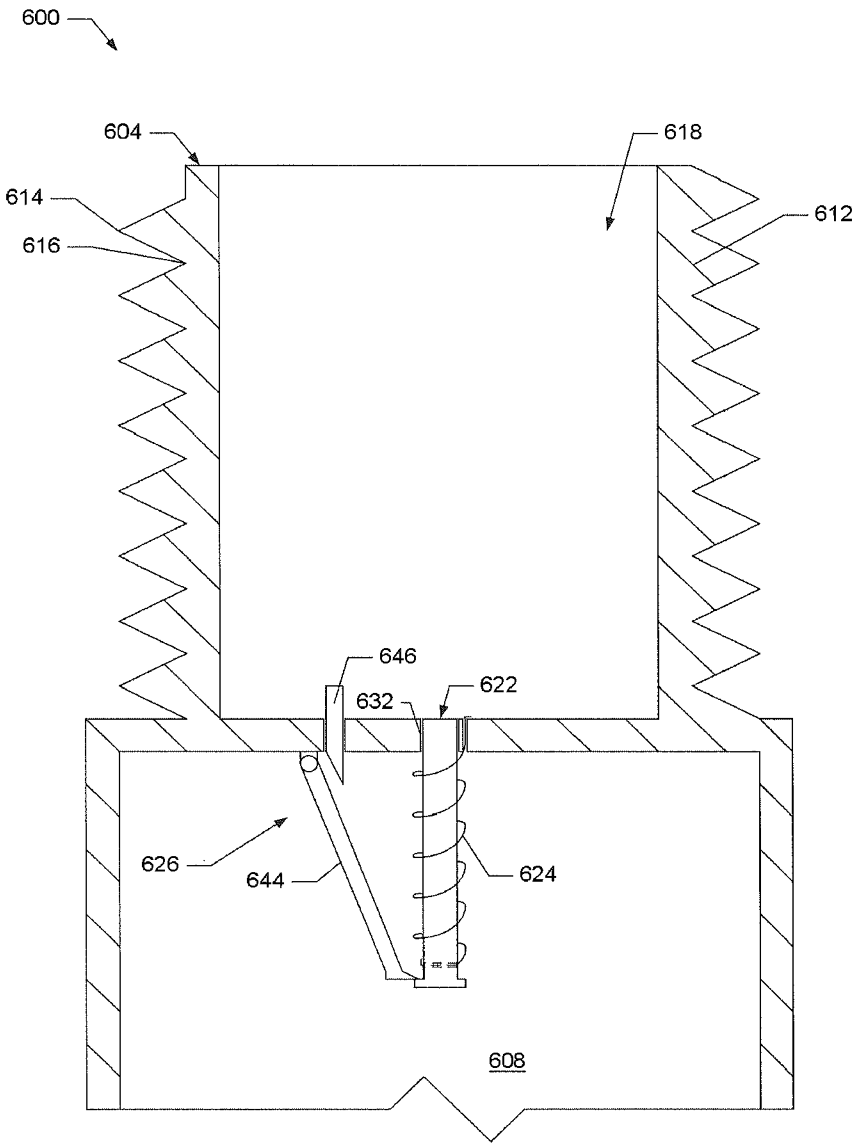
Figure 10:
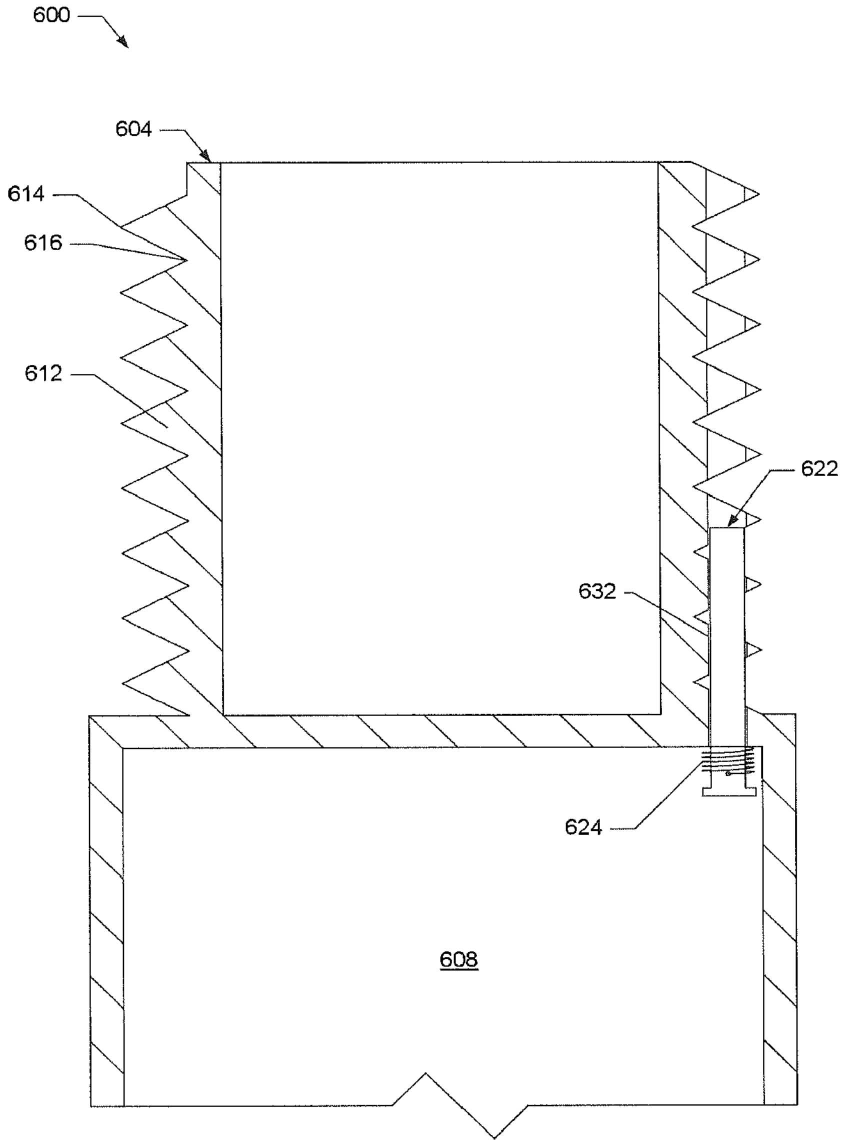
Figure 11:
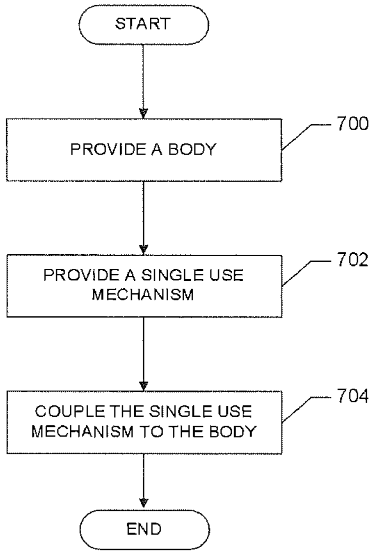

Having thus described the disclosure in the foregoing general terms, reference will now be made to the accompanying drawings, which are not necessarily drawn to scale, and wherein:

FIG. 1 illustrates a sectional view through an embodiment of a smoking article comprising a control body and a cartridge according to an embodiment of the present disclosure;

FIG. 2 illustrates an embodiment of a single-use cartridge including a threaded connector at an inner surface thereof according to an embodiment of the present disclosure:

FIG. 3 illustrates a view of a distal attachment end of the cartridge of FIG. 2 according to an example embodiment of the present disclosure;

FIG. 4 illustrates a partial cut-away view through the cartridge of FIG. 2 along line 4-4 with a blocking pin of a single-use mechanism thereof configured in a retracted position according to an example embodiment of the present disclosure;

FIG. 5 illustrates a partial cut-away view through the cartridge of FIG. 2 along line 4-4 during engagement with a mating connector according to an example embodiment of the present disclosure;

FIG. 6 illustrates a partial cut-away view through the cartridge of FIG. 2 along line 4-4 after disengagement from the mating connector such that the blocking pin of the single-use mechanism thereof is configured in an extended position according to an embodiment of the present disclosure;

FIG. 7 illustrates a partial cut-away view through the cartridge of FIG. 2 along line 7-7 after disengagement from the mating connector such that the blocking pin of the single-use mechanism thereof is configured in an extended position according to an embodiment of the present disclosure;

FIG. 8 illustrates a view of a distal attachment end of a cartridge defining a threaded connector on an outer surface thereof according to an example embodiment of the present disclosure;

FIG. 9 illustrates a partial cut-away view through the cartridge of FIG. 8 along line 9-9 with a blocking pin of a single-use mechanism thereof configured in a retracted position according to an example embodiment of the present disclosure;

FIG. 10 illustrates a partial cut-away view through the cartridge of FIG. 8 along line 10-10 after disengagement from a mating connector such that the blocking pin of the single-use mechanism thereof is configured in an extended position according to an embodiment of the present disclosure; and FIG. 11 schematically illustrates a method for assembling a connector according to an example embodiment of the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms “a”, “an”, “the”, include plural referents unless the context clearly dictates otherwise.

The present disclosure relates to articles that use electrical energy to heat a material (preferably without combusting the material to any significant degree) to form an inhalable substance, the articles being sufficiently compact to be considered “hand-held” devices. In certain embodiments, the articles can particularly be characterized as smoking articles. As used herein, the term is intended to mean an article that provides the taste and/or the sensation (e.g., hand-feel or mouth-feel) of smoking a cigarette, cigar, or pipe without substantial combustion of any component of the article. The term smoking article does not necessarily indicate that, in operation, the article produces smoke in the sense of the by-product of combustion or pyrolysis. Rather, smoking relates to the physical action of an individual in using the article—e.g., holding the article, drawing on one end of the article, and inhaling from the article. In further embodiments, the articles to which the present disclosure relates can be characterized as being vapor-producing articles, aerosolization articles, or medicament delivery articles. Thus, the articles can be arranged so as to provide one or more substances in an inhalable state. In other embodiments, the inhalable substance can be substantially in the form of a vapor (i.e., a substance that is in the gas phase at a temperature lower than its critical point). In other embodiments, the inhalable substance can be in the form of an aerosol (i.e., a suspension of fine solid particles or liquid droplets in a gas). The physical form of the inhalable substance is not necessarily limited by the nature of the articles but rather may depend upon the nature of the medium and the inhalable substance itself as to whether it exists in a vapor state or an aerosol state. In some embodiments, the terms may be interchangeable. Thus, for simplicity, the terms as used to describe the articles are understood to be interchangeable unless stated otherwise.

In one aspect, the present disclosure provides a smoking article. The smoking article generally can include a number of components provided within an elongated body, which can be a single, unitary shell or body or which can be formed of two or more separable pieces. For example, a smoking article according to one embodiment can comprise a shell (i.e., the elongated body) that can be substantially tubular in shape, such as resembling the shape of a conventional cigarette or cigar. Within the shell can reside all of the components of the smoking article (one or more of which may be replaceable). In other embodiments, a smoking article can comprise two shells that are joined and are separable. For example, a control body can comprise a shell containing one or more reusable components and having an end that removably attaches to a cartridge. The cartridge can comprise a shell containing one or more disposable components and having an end that removably attaches to the control body. More specific arrangements of components within the single shell or within the separable control body and cartridge are evident in light of the further disclosure provided herein.

Smoking articles useful according to the disclosure particularly can comprise some combination of a power source (i.e., an electrical power source), one or more control components (e.g., to control/actuate/regulate flow of power from the power source to one or more further components of the article), a heater component, and an aerosol precursor component. The smoking article further can include a defined air flow path through the article such that aerosol generated by the article can be withdrawn therefrom by a user drawing on the article. Alignment of the components within the article can vary. In specific embodiments, the aerosol precursor component can be located near an end of the article that is proximal to the mouth of a user so as to maximize aerosol delivery to the user. Other configurations, however, are not excluded. Generally, the heater component can be positioned sufficiently near the aerosol precursor component so that heat from the heater component can volatilize the aerosol precursor (as well as one or more flavorants, medicaments, or the like that may likewise be provided for delivery to a user) and form an aerosol for delivery to the user. When the heating member heats the aerosol precursor component, an aerosol (alone or including a further inhalable substance) is formed, released, or generated in a physical form suitable for inhalation by a consumer. It should be noted that the foregoing terms are meant to be interchangeable. As such, the terms release, generate, and form can be interchangeable, the terms releasing, generating, and forming can be interchangeable, the terms releases, forms, and generates can be interchangeable, and the terms released, formed, and generated can be interchangeable. Specifically, an inhalable substance is released as a vapor or aerosol or mixture thereof.

An exemplary smoking article 10 according to the disclosure is shown in FIG. 1. As seen in the cross-section illustrated therein, the smoking article 10 can comprise a control body 80 and a cartridge 90 that can be aligned in a functioning relationship. In this regard, the control body 80 and the cartridge 90 may be attachable and detachable from each other. Although a threaded engagement is illustrated in FIG. 1, it is understood that further means of engagement are encompassed, such as a press-fit engagement, a magnetic engagement, or the like. The cartridge can particularly include a single use connector as otherwise described herein.

In specific embodiments, the control body 80 may be referred to as being reusable, and the cartridge 90 may be referred to as being disposable. In some embodiments, the entire smoking article may be characterized as being disposable in that the control body may be configured for only a limited number of uses (e.g., until a battery power component no longer provides sufficient power to the smoking article) with a limited number of cartridges and, thereafter, the entire smoking article 10, including the control body, may be discarded. In other embodiments, the control body may have a replaceable battery such that the control body can be reused through a number of battery exchanges and with many cartridges. Similarly, the smoking article 10 may be rechargeable and thus may be combined with any type of recharging technology, including connection to a typical electrical outlet, connection to a car charger (i.e., cigarette lighter receptacle), and connection to a computer, such as through a USB cable.

The control body 80 includes a control component 20, a flow sensor 30, and a battery 40. Although these components are illustrated in a specific alignment, it is understood that various alignments of the components are encompassed by the present disclosure. The control body 80 further includes a plurality of indicators 19 at a distal end 12 of the control body shell 81. Such indicators 19, as discussed above, can show the number of puffs taken or remaining from the smoking article, can be indicative of an active or inactive status, can light up in response to a puff, or the like. The indicators can be provided in varying numbers and can take on different shapes and can even being simply an opening in the body (such as for release of sound when such indicators are present).

Various positions for one or more air intakes 17 are encompassed by the present disclosure. As shown, the air intake 17 may be positioned in the control body shell 81 such that air drawn through the intake sufficiently contacts the flow sensor 30 to activate the sensor (although other positions are encompassed, particularly if different sensing means are provided or if manual actuation, such as with a push button, is provided). A receptacle 60 also is included at the proximal attachment end 13 of the control body 80 and extends into the control body projection 82 to allow for ease of electrical connection with the resistive heating element 50 when the cartridge 90 is attached to the control body. In the illustrated embodiment, the receptacle 60 includes a central open passage to facilitate air flow from the air intake in the control body into the cartridge during use of the article 10.

The cartridge 90 includes a cartridge shell 91 with a mouth opening 18 at the mouthend 11 thereof to allow passage of air and entrained vapor (i.e., the components of the aerosol precursor composition in an inhalable form) from the cartridge to a consumer during draw on the smoking article 10. The smoking article 10 according to the present disclosure may have an overall shape that may be defined as being substantially rod-like or substantially tubular shaped or substantially cylindrically shaped. As illustrated in FIG. 1, the smoking article 10 has a substantially round cross-section; however, other cross-sectional shapes (e.g., oval, square, triangle, etc.) also are encompassed by the present disclosure. Such language that is descriptive of the physical shape of the smoking article may also be applied to the individual units of the smoking article in embodiments comprising multiple units, such as a control body and a cartridge.

In preferred embodiments, the smoking article 10 may take on a size that is comparative to a cigarette or cigar shape. Thus, the smoking article may have a diameter of about 5 mm to about 25 mm, about 5 mm to about 20 mm, about 6 mm to about 15 mm, or about 6 mm to about 10 mm Such dimension may particularly correspond to the outer diameter of the control body shell 81 and/or the cartridge shell 91. The control body can have a length of about 50 mm to about 110 mm, about 60 mm to about 100 mm, or about 65 mm to about 95 mm. The cartridge can have a length of about 20 mm to about 60 mm, about 25 mm to about 55 mm, or about 30 mm to about 50 mm. The overall length of the combined cartridge and control body (or the overall length of a smoking article according to the disclosure formed of a single, unitary shell) can be approximately equal to or less than the length of a typical cigarette—e.g., about 70 mm to about 130 mm, about 80 mm to about 125 mm, or about 90 mm to about 120 mm.

The cartridge shell 91 of the smoking article 10 can be formed of any material suitable for forming and maintaining an appropriate conformation, such as a tubular shape, and for retaining therein the suitable components of the smoking article. The body can be formed of a single wall, as shown in FIG. 1. The cartridge shell 91 can be formed of a material (natural or synthetic) that is heat resistant so as to retain its structural integrity—e.g., does not degrade—at least at a temperature that is the heating temperature provided by the resistive heating element. In some embodiments, a heat resistant polymer may be used. In other embodiments, the body can be formed from paper, such as a paper that is substantially straw-shaped, or from metal, such as stainless steel. As further discussed herein, the body, such as a paper tube, may have one or more layers associated therewith that function to substantially prevent movement of vapor therethrough. In one example, an aluminum foil layer may be laminated to one surface of the body. Ceramic materials also may be used.

The cartridge 90 further includes a resistive heating element 50 in the form of a metal wire coil. The resistive heating element includes terminals 51 (e.g., positive and negative terminals) at the opposing ends thereof for facilitating current flow through the resistive heating element and for attachment of the appropriate wiring (not illustrated) to form an electrical connection of the resistive heating element with the battery 40 when the cartridge 90 is connected to the control body 80. Specifically, a plug 65 is positioned at the distal attachment end 14 of the cartridge. When the cartridge 90 is connected to the control body 80, the plug 65 engages the receptacle 60 to form an electrical connection such that current controllably flows from the battery 40, through the receptacle and plug, and to the resistive heating element 50. The cartridge shell 91 can continue across the distal attachment end such that this end of the cartridge is substantially closed with the plug protruding therefrom. As illustrated in FIG. 1, the plug 65 includes an open central passage that aligns with the open central passage in the receptacle 60 to allow air to flow from the control body 80 and into the cartridge 90.

Generally, in use, when a consumer draws on the mouthend 11 of the cartridge, the flow sensor 30 detects the change in flow and activates the control component 20 to facilitate current flow through the resistive heating element 50. Thus, it is useful for air flow to travel through the control body 80 in a manner that flow sensor 30 detects air flow almost instantaneously.

The control algorithm may call for power to the resistive heating element 50 to cycle and thus maintain a defined temperature. The control algorithm therefore can be programmed to automatically deactivate the smoking article 10 and discontinue power flow through the smoking article after a defined time lapse without a puff by a consumer. Moreover, the smoking article can include a temperature sensor to provide feedback to the control component. Such sensor can be, for example, in direct contact with the resistive heating element 50. Alternative temperature sensing means likewise may be used, such as relying upon logic control components to evaluate resistance through the resistive heating element and correlate such resistance to the temperature of the element. In other embodiments, the flow sensor 30 may be replaced by appropriate components to provide alternative sensing means, such as capacitive sensing. Still further, one or more control buttons can be included to allow for manual actuation by a consumer to elicit a variety of functions, such as powering the article 10 on and off, turning on the heating element 50 to generate a vapor or aerosol for inhalation, or the like.

When the flow sensor 30 is positioned within the control body 80, it can be useful to have an air intake 17 on the control body. If desired, a sealed flow path can be provided such that the flow sensor 30 within the control body 80 is in fluid connection with the cartridge interior after the cartridge and the control body are engaged, such fluid connection being sealed with respect to the remainder of the components within the control body but opening into the cartridge 90 when attached to the control body. Further, in other embodiments, the flow sensor 30 can be located within the cartridge 90 instead of the control body 80.

A reservoir may utilize a transport element to transport an aerosol precursor composition to an aerosolization zone. One such example is shown in FIG. 1. As seen therein, the cartridge 90 includes a reservoir layer 201 comprising layers of nonwoven fibers formed into the shape of a tube encircling the interior of the cartridge shell 91, in this embodiment. An aerosol precursor composition is retained in the reservoir layer 201. Liquid components, for example, can be sorptively retained by the reservoir layer 201. The reservoir layer 201 is in fluid connection with a transport element 301 (a wick in this embodiment). The wick 301 transports the aerosol precursor composition stored in the reservoir layer 201 via capillary action to an aerosolization zone 400 of the cartridge 90. As illustrated, the wick 301 is in direct contact with the resistive heating element 50 that is in the form of a metal wire coil in this embodiment.

In use, when a user draws on the article 10, the resistive heating element 50 is activated (e.g., such as via a puff sensor), and the components for the aerosol precursor composition are vaporized in the aerosolization zone 400. Drawing upon the mouthend 11 of the article 10 causes ambient air to enter the air intake 17 and pass through the central opening in the receptacle 60 and the central opening in the plug 65. In the cartridge 90, the drawn air passes through an air passage 230 in an air passage tube 220 and combines with the formed vapor in the aerosolization zone 400 to form an aerosol. The aerosol is whisked away from the aerosolization zone, passes through an air passage 260 in an air passage tube 250, and out the mouth opening 18 in the mouthend 11 of the article 10.

The smoking article 10 in the embodiment illustrated in FIG. 1 can be characterized as a disposable article. Accordingly, it can be desirable for the reservoir layer 201 in such embodiments to include a sufficient amount of aerosol precursor composition and any further inhalable materials (which may separately be provided on a different substrate) so that a consumer can obtain more than a single use of the smoking article. For example, the smoking article can include sufficient aerosolizable and/or inhalable materials such that the smoking article can provide a number of puffs substantially equivalent to the number of puffs (of about two seconds duration) available from a plurality of conventional cigarettes—e.g., 2 or more, 5 or more, 10 or more, or 20 or more conventional cigarettes. More particularly, a disposable, single unit article according to the embodiment of FIG. 1 can provide about 20 or more, about 50 or more, or about 100 or more puffs.

Although FIG. 1 is illustrative of a smoking article according to the present disclosure, the scope of the disclosure should not be viewed as being limited to the specific combination and/or arrangement of components illustrated therein. Rather, the present disclosure can encompass a variety of combinations of components useful in forming an electronic smoking article. Reference is made for example to the smoking articles disclosed in U.S. patent application Ser. No. 13/536,438, filed Jun. 28, 2012, and U.S. patient application Ser. No. 13/432,406, filed Mar. 28, 2012, the disclosures of which are incorporated herein by reference in their entirety. Further to the above, representative heating element and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

The various components of a smoking article according to the present invention can be chosen from components described in the art and commercially available. Examples of batteries that can be used according to the disclosure are described in U.S. Pub. App. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers, that can be useful in the present smoking article are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

The aerosol precursor, which may also be referred to as a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. I Reynolds Tobacco Company Monograph (1988); the disclosures of which are incorporated herein by reference.

Still further components can be utilized in the smoking article of the present disclosure. For example, U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. 2009/0320863 by Fernando et al. discloses computer interfacing means for smoking devices to facilitate charging and allow computer control of the device; U.S. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Pub. Nos. 2009/0095311, 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon. A variety of the materials disclosed by the foregoing documents may be incorporated into the present devices in various embodiments, and all of the foregoing disclosures are incorporated herein by reference in their entireties.

Although an article according to the disclosure may take on a variety of embodiments, as discussed in detail below, the use of the article by a consumer will be similar in scope. In particular, the article can be provided as a single unit or as a plurality of components that are combined by the consumer for use and then are dismantled by the consumer thereafter. Generally, a smoking article according to the disclosure can comprise a first unit that is engagable and disengagable with a second unit, the first unit comprising the resistive heating element, and the second unit comprising the electrical power source. In some embodiments, the second unit further can comprise one or more control components that actuate or regulate current flow from the electrical power source. The first unit can comprise a distal end that engages the second unit and an opposing, proximate end that includes a mouthpiece (or simply the mouthend) with an opening at a proximate end thereof. The first unit can comprise an air flow path opening into the mouthpiece of the first unit, and the air flow path can provide for passage of aerosol formed from the resistive heating element into the mouthpiece. In preferred embodiments, the first unit can be disposable. Likewise, the second unit can be reusable.

During use, the consumer initiates heating of the resistive heating element, the heat produced by the resistive heating element aerosolizes the aerosol precursor composition and, optionally, further inhalable substances. Such heating releases at least a portion of the aerosol precursor composition in the form of an aerosol (which can include any further inhalable substances included therewith), and such aerosol is provided within a space inside the cartridge that is in fluid communication with the mouthend of the cartridge. When the consumer inhales on the mouth end of the cartridge, air is drawn through the cartridge, and the combination of the drawn air and the aerosol is inhaled by the consumer as the drawn materials exit the mouth end of the cartridge (and any optional mouthpiece present) into the mouth of the consumer. To initiate heating, the consumer may actuate a pushbutton, capacitive sensor, or similar component that causes the resistive heating element to receive electrical energy from the battery or other energy source (such as a capacitor). The electrical energy may be supplied for a pre-determined length of time or may be manually controlled. Preferably, flow of electrical energy does not substantially proceed in between puffs on the article (although energy flow may proceed to maintain a baseline temperature greater than ambient temperature—e.g., a temperature that facilitates rapid heating to the active heating temperature). In further embodiments, heating may be initiated by the puffing action of the consumer through use of various sensors, as otherwise described herein. Once the puff is discontinued, heating will stop or be reduced. When the consumer has taken a sufficient number of puffs so as to have released a sufficient amount of the inhalable substance (e.g., an amount sufficient to equate to a typical smoking experience), the cartridge can be removed from the control housing and discarded. Indication that the cartridge is spent (i.e., the aerosol precursor composition has been substantially removed by the consumer) can be provided. In some embodiments, a single cartridge can provide more than a single smoking experience and thus may provide a sufficient content of aerosol precursor composition to simulate as much as full pack of conventional cigarettes or even more.

The foregoing description of use of the article can be applied to the various embodiments described through minor modifications, which can be apparent to the person of skill in the art in light of the further disclosure provided herein. The above description of use, however, is not intended to limit the use of the article but is provided to comply with all necessary requirements of disclosure of the present disclosure.

Applicant has determined that it may be desirable to prevent re-use of cartridges for smoking articles in some instances. In this regard, it may be desirable to prevent refilling of cartridges to ensure that a user or a third-party does not refill the cartridge with a product that differs in quality or composition from the components originally stored therein. Accordingly, issues with respect to confusion regarding the contents of a cartridge may be avoided, and various other benefits may be provided.

In this regard, FIG. 2 illustrates an embodiment of a single-use cartridge 500 in accordance with an example embodiment of the disclosure. The cartridge 500 may be employed with any of a variety of smoking articles, including the smoking articles discussed above. In this regard, the cartridge 500 may include a connector 502 at a distal attachment end 504 that may be configured to engage a control body of a smoking article. The connector 502 may comprise a single-use connector, as described below.

A mouth opening 506 may be in communication with a chamber 508 configured to hold a product 509 such as an aerosol precursor composition, which may be stored in a reservoir layer as described above. The mouth opening 506 may be provided at a mouth end 510 of the cartridge 500. Various other components described above with respect to the example embodiments of smoking articles may be included in the cartridge 500. For example, the cartridge 500 may also include a resistive heating element with corresponding electrical terminals and a wick for directing the product 509 to the resistive heating element. In further embodiments, various other components not presently illustrated may be included therein.

Turning now to FIG. 3, a view of the distal attachment end 504 of the cartridge 500 is provided. As illustrated, the connector 502 may include a shell or body 512 comprising a plurality of threads 514 and a plurality of recesses 516 respectively positioned between the threads. The threads 514 and recesses 516 are defined at an inner surface of the body 512 and surround a cavity 518 configured to receive a mating connector (e.g., a control body projection) of a corresponding control body or other device. The connector 502 also includes a single-use mechanism 520, as discussed below.

FIG. 4 illustrates a partially cut-away view through the body 512 of the cartridge 500 along line 4-4 in FIG. 3. As illustrated in FIG. 4, the single-use mechanism 520 may comprise a blocking pin 522, a biasing mechanism 524, and a release mechanism 526. The operation of the single-use mechanism 520 will be described in detail below. Briefly, however, the blocking pin 522 may be configurable between a retracted position (see, e.g., FIG. 4) and an extended position (see, e.g., FIG. 6). The biasing mechanism 524 may be configured to bias the blocking pin 522 toward the extended position. The release mechanism 526 may be configured to retain the blocking pin 522 in the retracted position and release the blocking pin after the threads 514 and recesses 516 of the connector 502 engage a mating connector.

The blocking pin 522 may comprise a shaft 528 and a head 530. The shaft 528 of the blocking pin 522 may be received in an aperture 532 defined in the body 512 of the cartridge 500. As discussed in detail below, the aperture 532 may extend through one or more of the threads 514 of the body 512. However, in the retracted position, the blocking pin 522 may be at least partially retracted from the aperture 532 such that the blocking pin does not block the recesses 516 between the threads 514.

The biasing mechanism 524 may comprise a spring (e.g., a coil spring), which may be coupled at a first end 534 to a divider wall 536 at least partially separating the connector 502 from the chamber 508 in which the product 509 may be stored. Although not illustrated, apertures for air flow therethrough, terminals for electric connection, and/or other components may be provided at and through the divider wall 536 such that connection with a control body may allow for operation as described above. In one embodiment, the first end 534 of the biasing mechanism 524 may be received through an aperture 538 in the divider wall 534. A second end 540 of the biasing mechanism 524 may be coupled to the blocking pin 522. For example, the second end 540 of the biasing mechanism 524 may be received through an aperture 542 defined through the blocking pin 522.

The release mechanism 526 may comprise a latch 544 and a release pin 546. The latch 544 may be configured to engage the blocking pin 522 and retain the blocking pin in the retracted position. For example, the latch 544 may comprise a first end defining an extension 548 configured to engage the head 530 of the blocking pin 522. A second end of the latch 544 may comprise a hinge 550 that is coupled to the divider wall 536. Alternatively, the latch 544 may be formed from a bendable material that allows the latch to bend and pivot.

As illustrated in FIG. 5, the connector 502 may be configured to engage a mating connector 552 (e.g., a control body projection) of a control body 554, or other smoking article or portion thereof. The release mechanism 526 may be configured to release the blocking pin 522 after the threads 514 and recesses 516 of the connector 502 engage corresponding threads 556 and recesses 558 of the mating connector 552.

In this regard, the release pin 546 may be configured to release the latch 544 from engagement with the blocking pin 522. More particularly, an end 560 of the mating connector 552, or a thread 556 thereof proximate the end, may press against a first end 562 of the release pin 546 when the threads 514 and recesses 516 of the connector 502 engage the threads 556 and recesses 558 of the mating connector during attachment of the connector to the mating connector. Accordingly, the release pin 546 may be displaced inwardly toward the chamber 508.

Note that although the release pin 546 is illustrated as being received in an aperture 564 which extends through the threads 514 (see, e.g., FIG. 3), the release pin may extend into the aperture 564 a relatively short distance such that the release pin does not block any of the recesses 516 defined by the connector 502, and thereby the mating connector 552 may fully engage the threads 514 and recesses 516 thereof. However, in an alternate embodiment, as illustrated in phantom in FIG. 3, an alternate embodiment of a release pin 546' and a corresponding aperture 564' may not extend through the threads 514. Thereby, issues with respect to the release pin preventing the mating connector 552 from fully engaging the connector 502 may be avoided in a variety of manners.

As the release pin 546 is displaced toward the chamber 508, a tapered end 566 of the release pin may engage the latch 544. The tapered end 566 may be configured to reduce the possibility of binding between the latch 544 and the release pin 546 that may occur if the release pin were to include a blunt end with a sharp edge that engages the latch. By engaging the latch 544, the release pin 546 may pivot the latch out of contact with the head 530 of the blocking pin 522 either by pivoting the latch about the hinge 550 or by bending the latch.

Accordingly, the biasing mechanism 524 may bias the blocking pin 522 against the end 560 of the mating connector 552 (or a thread 556 thereof proximate the end). Thus, as the connector 502 of the cartridge 500 is unscrewed from the mating connector 552 of the control body 554, the blocking pin 522 may extend outwardly into the cavity 518 of the connector 502, until the blocking pin reaches an extended position, as illustrated in FIG. 6. In this regard, a user may remove the cartridge 500 from the control body 554 after the product 509 in the chamber 508 has been expended through use.

As illustrated in FIG. 7, which is a partially cut-away view through the body 512 of the cartridge 500 along line 7-7 in FIG. 3, in the extended position the blocking pin 522 may extend through the aperture 532 in the body 512 and block at least one of the recesses 516. For example, in the illustrated embodiment recesses 516*a-c* are blocked. Accordingly, if a user were to attempt to engage the cartridge 500 with the control body 554 for a second time, the blocking pin 522 would prevent re-engagement therewith. More particularly, the blocking pin 522 would prevent the threads 558 of the mating connector 552 from engaging the recesses 516*a-c* of the connector 502, such that the cartridge 500 may not fully engage the control body 554. Thereby, the cartridge may not establish electrical connections, and/or the other connections described above between a control body and a cartridge, such that the cartridge may not be reused.

Note that the aperture 532 may not extend all the way through to the distal attachment end 504 of the body 512 in all embodiments. In this regard, the aperture 532 may extend a short distance past the end of the blocking pin 522 in the extended position (e.g., with the aperture extending one or two threads past the last recess 516*c* blocked by the blocking pin). This embodiment may be preferable because it may hide the aperture 532 from view.

As noted above, in one embodiment of the present disclosure, the single-use connector may include threads and recesses defined at an inner surface of a body. Thus, the connector may be referred to as a female connector. However, in another embodiment of the disclosure the single-use connector may be referred to as a male connector.

In this regard, FIGS. 8-11 illustrate an alternate embodiment of a single-use cartridge 600. The cartridge 600 illustrated in FIGS. 8-11 may be substantially similar to the cartridge 500 illustrated in FIGS. 3-8, with the exception of the external, instead of internal, configuration of the threads and recesses of the connector. Accordingly, the cartridge 600 will not be described in detail.

Briefly, however, FIG. 8 illustrates a view of a connector 602 at a distal attachment end 604 of the cartridge 600. A chamber 608 may be provided at an opposing end of the cartridge 600 (see, e.g., FIG. 9). As illustrated, the connector 602 may include a body 612 comprising a plurality of threads 614 and a plurality of recesses 616 respectively positioned between the threads. The threads 614 and recesses 616 are defined at an outer surface of the body 612 and may surround a cavity 618 in some embodiments. The threads 614 and recesses 616 may be received in a cavity defined by a mating connector of a control body during connection therewith. The connector 602 also includes a single-use mechanism 620.

FIG. 9 illustrates a partially cut-away view through the body 612 of the cartridge 600 along line 9-9 in FIG. 8. As illustrated in FIG. 9, the single-use mechanism 620 may comprise a blocking pin 622, a biasing mechanism 624, and a release mechanism 626. As described above, the blocking pin 622 may be configurable between a retracted position (see, e.g., FIG. 9) and an extended position (see, e.g., FIG. 10). The biasing mechanism 624 may be configured to bias the blocking pin 622 toward the extended position. The blocking pin 622 may be received in an aperture 632 extending through one or more of the threads 614.

The release mechanism 626 may be configured to retain the blocking pin 622 in a retracted position and release the blocking pin after the threads 614 and recesses 616 of the connector 602 engage a mating connector. In this regard, the release mechanism 616 may comprise a latch 644 that is released from engagement with the blocking pin 622 by a release pin 646 after the threads 614 and recesses 616 of the connector 602 engage corresponding threads and recesses of a mating connector. Accordingly, as illustrated in FIG. 10, which is a partially cut-away view through the body 612 of the cartridge 600 along line 10-10 in FIG. 8, the blocking pin 622 may be displaced by the biasing mechanism 624 to an extended position in which the blocking pin extends through the aperture 632 and blocks at least one of the recesses 616. Thereby, reuse of the cartridge 600 may be resisted as described above. As described above, although illustrated as extending to the distal attachment end 604, in other embodiments the aperture 632 may not extend all the way to the distal attachment end in order to at least partially hide the aperture from a user's view in some embodiments.

Note also that various other embodiments of single-use mechanisms employing blocking pins that extend through one or more threads of a connector after use thereof may be employed in the embodiments of single-use cartridges described herein. In this regard, the embodiments of biasing and release mechanisms described herein are provided for example purposes only. Further, although the connectors including single-use mechanisms are generally described herein as defining portions of cartridges configured for connection to control bodies, in other embodiments the connectors including single-use mechanisms may comprise portions of control bodies. In this regard, in some embodiments it may be desirable to prevent re-use of a control body. Accordingly, it should be understood that the particular embodiments of connectors with single-use mechanisms described above are provided for example purposes only.

A method for assembling a connector is also provided. As illustrated in FIG. 11, the method may include providing a body at operation 700. The body may define a plurality of threads, a plurality of recesses, and an aperture extending through one or more of the threads. The method may additionally include providing a single-use mechanism at operation 702. The single-use mechanism may comprise a blocking pin, a release mechanism, and a biasing mechanism. Further, the method may include coupling the single-use mechanism to the body at operation 704. Coupling the single-use mechanism to the body at operation 704 may be conducted such that the blocking pin is in a retracted position wherein the blocking pin is at least partially retracted from the aperture by the release mechanism, wherein upon disengagement of the threads and recesses from a mating connector the release mechanism releases the blocking pin and the biasing mechanism biases the blocking pin to an extended configuration in which the blocking pin extends through the aperture and blocks at least one of the recesses.

In some embodiments coupling the single-use mechanism to the body at operation 704 may comprise coupling a coil spring to the body and the blocking pin. Coupling the single-use mechanism to the body at operation 704 may further comprise retracting the blocking pin to the retracted position and engaging the blocking pin with a latch. Coupling the single-use mechanism to the body at operation 704 may additionally include positioning a release pin in an extended position configured to engage the mating connector and release the latch from the blocking pin upon engagement therewith.

Although the cartridge and the control body can be provided together as a complete smoking article or medicament delivery article generally, the components also may be provided separately. For example, the disclosure also encompasses a disposable cartridge unit for use with a reusable smoking article or a reusable medicament delivery article (e.g., a smoking article control body).

In another aspect, the disclosure can be directed to kits that provide a variety of components as described herein. For example, a kit can comprise a control body with one or more cartridges. A kit further can comprise a control body with one or more charging components. A kit further can comprise a control body with one or more batteries. A kit further may comprise a control body with one or more cartridges and one or more charging components and/or one or more batteries. In further embodiments, a kit may comprise a plurality of cartridges. A kit further may comprise a plurality of cartridges and one or more batteries and/or one or more charging components. The kits further can include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims.

Although specific terms are employed herein, they are used in a generic and descriptive sense only and not for purposes of limitation.

The invention claimed is:

1. An electronic smoking article, comprising:

a single-use cartridge, comprising:

a chamber configured to hold a product; and a connector, comprising:

a body, defining:

a plurality of threads;

a plurality of recesses respectively positioned between the threads; and an aperture extending through one or more of the threads; and a single-use mechanism, comprising:

a blocking pin configurable between a retracted position in which the blocking pin is at least partially retracted from the aperture and an extended position in which the blocking pin extends through the aperture and blocks at least one of the recesses;

a biasing mechanism configured to bias the blocking pin toward the extended position; and a release mechanism configured to retain the blocking pin in the retracted position and release the blocking pin after the threads and the recesses engage corresponding threads and recesses of a mating connector.

2. The electronic smoking article of claim 1, wherein the threads and the recesses are defined at an inner surface of the body surrounding a cavity configured to receive the mating connector.

3. The electronic smoking article of claim 1, wherein the threads and the recesses are defined at an outer surface of the body and configured to be received in a cavity defined by the mating connector.

4. The electronic smoking article of claim 1, wherein the release mechanism comprises:

a latch configured to engage the blocking pin to retain the blocking pin in the retracted position; and a release pin configured to release the latch from engagement with the blocking pin.

5. The electronic smoking article of claim 4, wherein the blocking pin defines a head and the latch is configured to engage the head of the blocking pin and pivot out of contact therewith upon being displaced by the release pin.

6. The electronic smoking article of claim 5, wherein the release pin defines a tapered end configured to engage the latch.

7. The electronic smoking article of claim 6, wherein the release pin is configured to engage an end of the mating connector when the threads and the recesses engage the mating connector.

8. The electronic smoking article of claim 1, wherein the biasing mechanism comprises a coil spring.

9. The electronic smoking article of claim 1, wherein the product comprises an aerosol precursor composition.

* * * * *